(12) United States Patent
Borot de Battisti et al.

(10) Patent No.: US 10,933,254 B2
(45) Date of Patent: Mar. 2, 2021

(54) DEVICE AND METHOD FOR ASSISTING IN A BRACHYTHERAPY PROCEDURE

(71) Applicant: KONINKLIJKE PHILIPS N.V., Eindhoven (NL)

(72) Inventors: Maxence Borot de Battisti, Eindhoven (NL); Guillaume Leopold Theodorus Frederik Hautvast, Veldhoven (NL); Baudouin Denis de Senneville, Eindhoven (NL); Rien Moerland, Eindhoven (NL); Metha Maenhout, Eindhoven (NL); Dirk Binnekamp, Weerselo (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 350 days.

(21) Appl. No.: 15/754,015

(22) PCT Filed: Aug. 30, 2016

(86) PCT No.: PCT/EP2016/070410
§ 371 (c)(1),
(2) Date: Feb. 21, 2018

(87) PCT Pub. No.: WO2017/037060
PCT Pub. Date: Mar. 9, 2017

(65) Prior Publication Data
US 2018/0236263 A1    Aug. 23, 2018

(30) Foreign Application Priority Data

Sep. 1, 2015 (EP) .................................. 15183303

(51) Int. Cl.
*A61N 5/10* (2006.01)

(52) U.S. Cl.
CPC ......... *A61N 5/1007* (2013.01); *A61N 5/1001* (2013.01); *A61N 5/1027* (2013.01); *A61N 5/1031* (2013.01); *A61N 5/1038* (2013.01); *A61N 5/1049* (2013.01); *A61N 2005/101* (2013.01); *A61N 2005/1024* (2013.01)

(58) Field of Classification Search
CPC .......... A61N 5/1001–1029; A61N 5/103–1039
See application file for complete search history.

(56) References Cited

U.S. PATENT DOCUMENTS 5,391,139 A    2/1995  Edmundson
6,311,084 B1  10/2001  Cormack et al.
(Continued)

FOREIGN PATENT DOCUMENTS

WO    2014091330 A1   6/2014

*Primary Examiner* — Thaddeus B Cox
(74) *Attorney, Agent, or Firm* — Sherry Austin (57) ABSTRACT

The invention relates to a delivery assistance device for assisting in a brachytherapy procedure. The invention provides for an output of an optimized treatment plan, taking into considering the portions of the procedure already carried out. The invention provides for an update of the sequence and the dosing after, for example, each needle insertion. The sequence of the treatment plan is determined such that, for example, steps of the procedure in which an error may have a larger impact, which needs to be corrected by modifying later steps, are provided earlier than steps in which an error is less likely and/or may have a lesser impact.

14 Claims, 2 Drawing Sheets

(56) References Cited

U.S. PATENT DOCUMENTS

| | | |
|---|---|---|
| 6,530,873 B1 | 3/2003 | Lee |
| 2003/0065260 A1 | 4/2003 | Cheng et al. |
| 2008/0242914 A1 | 10/2008 | Henderson et al. |
| 2011/0288361 A1 | 11/2011 | Kindlein et al. |
| 2013/0102891 A1 | 4/2013 | Binnekamp et al. |
| 2014/0303423 A1 | 10/2014 | Amthor et al. |
| 2015/0119628 A1 | 4/2015 | Bharat et al. |
| 2017/0165500 A1* | 6/2017 | Flynn .................. A61N 5/1002 |

* cited by examiner

DEVICE AND METHOD FOR ASSISTING IN A BRACHYTHERAPY PROCEDURE

CROSS-REFERENCE TO PRIOR APPLICATIONS

This application is the U.S. National Phase application under 35 U.S.C. § 371 of International Application Serial No. PCT/EP2016/070410, filed on Aug. 30, 2016, which claims the benefit of European Patent Application No. 15183303.5, filed on Sep. 1, 2015. This application is hereby incorporated by reference herein.

FIELD OF THE INVENTION

The invention relates in general to the field of interventional oncology, in particular to a delivery assistance device for assisting in a brachytherapy procedure, a delivery system for brachytherapy including such delivery assistance device, a brachytherapy assistance method for assisting in a brachytherapy procedure and a corresponding computer program.

BACKGROUND OF THE INVENTION

In focal therapy of the prostate, for example, brachytherapy is used to treat the tumor only, sparing surrounding tissues. Compared to a traditional whole gland brachytherapy, focal brachytherapy is aimed to be equally effective, while reducing therapy side effects.

Examples of brachytherapy are low dose brachytherapy (LDR brachytherapy) and high dose brachytherapy (HDR brachytherapy). To determine LDR seed positions, or HDR dwell positions and dwell times, so-called inverse planning methods are used. These algorithms optimize the radiation dose, considering objectives for the target volume, as well as constraints with respect organs at risk, which are translated into a set of linear constraints for a linear system that is to be solved.

In an interventional oncology solution for the delivery of HDR brachytherapy, an ablation is performed by delivering a radiation dose by moving a highly active source through catheters that are positioned inside, or close to, the tumor tissue. The delivered dose is controlled by dwell positions along the catheter, as well as the dwell time spend in these positions. The HDR dose plan is computed given the regions of interest (ROIs) to be treated and their associated clinical objectives.

In an interventional oncology solution for the delivery of LDR brachytherapy, an ablation is performed by permanently placing small radioactive seeds inside, or close to, the tumor tissue. The delivered dose is thus controlled by positions of the seeds. An LDR dose plan is computed given the regions of interest (ROIs) to be treated and their associated clinical objectives.

A conventional procedure includes the steps of determining a dose plan, manually defining a needle sequence, selecting a needle and placing a needle. If not yet the last needle is placed, the flow returns to the selection of the needle, such that there is a loop of selecting a needle according to the needle sequence and placing the selected needle until the last needle is placed.

The results of such conventional procedure may be unsatisfactory. It may occur that a radiation dose is delivered that is slightly off compared to the originally computed plan, which ultimately may lead to less effective treatments or more short term side-effects.

Further, an assisting apparatus for assisting in performing a brachytherapy is disclosed in WO 2014/091330 A1, where in an updating of a treatment plan after placing a brachytherapy seed the already delivered radiation dose is taken into account, which is defined by the positions of the already placed brachytherapy seeds and there dwell times. The positions of the brachytherapy seeds that still need to be delivered to achieve prescribed radiation dose targets are determined based on the already delivered radiation dose.

SUMMARY OF THE INVENTION

It is an object of the present invention to provide delivery assistance for a brachytherapy procedure allowing for a close correspondence between an aim of the procedure or treatment objective and the result of the procedure, in particular in terms of the administered radiation dose.

In a first aspect of the present invention, a delivery assistance device is presented for assisting in a brachytherapy procedure, comprising an input unit arranged to receive information on a treatment objective, a planning unit arranged to determine a treatment plan based on the received information on the treatment objective, the treatment plan including dosage information for steps of the brachytherapy procedure, and an output unit arranged to output the determined treatment plan, wherein the treatment plan further includes sequence information for the steps of the brachytherapy procedure in the treatment plan indicating an order in which at least a subset of the steps of the brachytherapy procedure are to be carried out, wherein the planning unit is arranged to determine the sequence information so as to minimize an deviation expectation, indicating a deviation from the treatment objective to be expected, based on error expectation ranges of the steps of the brachytherapy procedure, wherein the input unit is further arranged to receive information on already provided steps of the brachytherapy procedure, wherein the planning unit is further arranged to determine a revised treatment plan based on the received information on the treatment objective and on the already provided steps of the brachytherapy procedure, and wherein the output unit is arranged to output the revised treatment plan.

In a second aspect of the present invention, a delivery system for brachytherapy is presented, comprising the delivery assistance device according to the first aspect, a brachytherapy control device and at least one brachytherapy instrument.

In a third aspect of the present invention, a brachytherapy assistance method is presented for assisting in a brachytherapy procedure, comprising an initial receiving step of receiving information on a treatment objective, a planning step of determining a treatment plan based on the received information on the treatment objective, the treatment plan including dosage information for steps of the brachytherapy procedure, and an initial output step of outputting the determined treatment plan, wherein the treatment plan further includes sequence information for the steps of the brachytherapy procedure in the treatment plan indicating an order in which at least a subset of the steps of the brachytherapy procedure are to be carried out, wherein the planning steps includes determining the sequence information so as to minimize an deviation expectation, indicating a deviation from the treatment objective to be expected, based on error expectation ranges of the steps of the brachytherapy procedure, wherein the method further comprises, after at least one step of the brachytherapy is provided, an additional receiving step of receiving information on already provided steps of the brachytherapy procedure, a revision step of determining a revised treatment plan based on the received information on the treatment objective and on the already provided steps of the brachytherapy procedure, wherein the revision step includes determining the sequence information of the revised treatment plan so as to minimize an deviation expectation, indicating a deviation from the treatment objective to be expected, based on error expectation ranges of the remaining steps of the brachytherapy procedure, and an additional output step of outputting the revised treatment plan.

It was found by the inventors that during placement of the needles according to the conventional procedure discussed above, there is no adaptive feedback on which needle to place next. As a consequence, clinicians perform needle placement while being blinded from the impact of a placement error in previous needles on the final dose plan and the impact of the next needle(s) on the final result. It may even occur that a clinician adhered to a needle sequence that is chosen to reduce image artifacts originating from the needles, rather than taking into account their impact on the resulting radiation dose.

In the context of WO 2014/091330, consideration is given to already placed brachytherapy seeds, so to update the treatment plan in an attempt to compensate for misplacements of brachytherapy seeds by adjusting future placement and/or dwell times.

It was found, however, by the inventors that there might be instances where a misplacement or wrong dwell time, for example, may not be compensated any more in the framework of the remaining steps of the brachytherapy. It was further realized by the inventors that different steps of the brachytherapy do not necessarily have the same impact in case errors may happen. Thus, the earlier a step in which an error may result in a strong impact or deviation is provided in the sequence, the more likely or easy it may be to compensate for such deviations by modifying the later steps.

The invention provides for an output of an optimized treatment plan, also taking into considering the portions of the procedure already carried out. The invention provides for an update of the sequence and the dosing after, for example, each needle insertion. The sequence of the treatment plan is determined such that, for example, steps of the procedure in which an error may have a larger impact, which needs to be corrected by modifying later steps, are provided earlier than steps in which an error is less likely and/or may have a lesser impact.

It is, however, not necessary that such update is provided after each and every step or portion of the procedure (even though combining steps without an update in between may result in a loss of accuracy and flexibility). Furthermore, the updating does not necessarily mean that there has to be a change in the treatment plan, as the existing treatment plan may already be preferable at the time.

Furthermore, the updating may result in just a change in the sequence (i.e. maintaining the previously determined dosage information), in just a change in the dosage (i.e. maintaining the previously determined sequence information) and in a combination of changing the sequence and the dosage information.

The error expectation ranges for the steps may be identical for all steps (e.g. assuming a positioning accuracy of ±1 mm for all placements or a timing accuracy of 1 second for all dwell times) or may be determined for each step, either individually or based on categories. In particular, the error expectation range may take into account positional accuracy, timing accuracy, as well as other accuracies and combinations thereof.

The deviation expectation is a measure for the amount of deviation which may eventually result in the brachytherapy procedure from the intended objective and indicates how close the eventual actual outcome may be to the desired outcome.

Considering a worst case scenario, one might assume that the first step in the procedure is carried out with an error or error consequence (i.e. a result of the error) at the border of which may reasonably expected, for example, in form of a misplacement of a brachytherapy seed. The following steps are modified to compensate but each again—in the worst case scenario—introduce some further individual misplacement (which again needs to be compensated by the remaining steps). In a recursive loop or process in which after each simulated step a further updating is provided (including a consideration of different sequences), a deviation expectation may be derived for such scenario.

The error expectation range may normally cover a continuum (e.g. a volume in space and a period in time (regarding dwell time and the like)) and depending on the particular implementation, such continuum may be addressed by a limited number of discrete points. A very coarse example in just one dimension may be the consideration of a placement 1 mm to far, a placement on the point and a placement 1 mm to short.

Another approach on the deviation expectation might consider each step separately, whereas a resulting deviation from the intended objective (e.g. dose) is determined (e.g. simulated) based on the assumption that the considered step includes the only error in the procedure and the remaining or following steps are modified to compensate for the error (without introducing errors themselves). In such approach a position of the step under consideration in the overall sequence may be determined in view of how many steps may still be needed for such compensation.

In an exemplary, but not limiting implementation of the invention in the context of HDR brachytherapy (see above), the inverse optimization allows for an optimal needle sequence that is presented to the user. The user places a needle, after which the impact of the placed needle on the delivered dose is to be assessed. If necessary, the dose plan is re-optimized including the computation of a new needle sequence. The new needle sequence is presented to the user. This process is repeated until the desired dose is delivered (i.e. the system no longer proposes to place a next needle).

The inventors have carried out simulations that have shown that re-optimization of HDR brachytherapy plans after needle insertion is beneficial to delivering the right radiation dose. In this exemplary implementation, the re-optimization considers already delivered doses as a give, such that only unexecuted dwell positions and dwell times and their sequence are modified if needed. In other words, the new needle sequence will always start with the already placed needles.

Updating or revising a treatment plan (e.g. sorting and selection of the needle sequence) may be performed during execution of the inverse optimization algorithms, by assessing the impact of the planned needles on the resulting dose, directly, and/or by assessing the impact of the planned needles on the resulting dose in a simulation incorporating needle positioning errors.

In another exemplary, but not limiting implementation of the invention in the context of LDR brachytherapy (see above), the re-optimization may result in a new sequence for placing the needles, as well as alternate loadings for some needles in the plan. Similar to the HDR example discussed above, the new needle sequence is presented to the user, who will keep on inserting needles until the desired dose is delivered (and the system no longer proposes to place a next needle). Here, the re-optimization only potentially modifies needle and seed positions that are not yet placed/delivered.

The updating of the treatment plan may include the removal of a previous provided step, if the treatment objective may already be achieved, or the addition of a further step, if needed or desirable to achieve the treatment objective.

In a preferred embodiment, the planning unit includes a calculation section for calculating a preliminary result from the information on already provided steps, a difference determination section for determining a difference between the preliminary result and the treatment objective, and a sub-plan determination section for determining a treatment sub-plan by means of inverse optimization on the determined difference, wherein the planning unit is arranged to determine the revised treatment plan by replacing the dosage information and sequence information for not yet provided steps according to the determined treatment sub-plan.

When taking into account already provided steps or portions of the procedure in revising or updating the treatment plan, the already provided steps or portions may be used as constraints (i.e. as fixed portions of the revised plan). Alternatively or in some combination, it is also possible to obtain the remaining treatment objective (i.e. that portion or part of the treatment objective not yet achieved by means of the already provided steps) and to determine a sub-plan only addressing the remaining objective (possibly taking into account constraints in the setup caused by the already executed steps), so that only the not yet executed portion of the treatment plan is replaced by the determined sub-plan.

The next step of the procedure (e.g. needle to be placed) can be indicated to the user in various ways, including, but not limited to using a graphical highlight in a list, using a graphical highlight on a rendering of a grid template, using dedicated lighting on the actual grid template and using orientation guidance in portal/key-hole approaches.

The actual inverse plan may be computed using any known optimization algorithm. This algorithm may include optimizing needle position and sequences directly.

In a preferred embodiment, the planning unit includes a deviation calculation section for calculating the deviation expectation for a treatment plan in view of the treatment objective according to a predetermined metric.

In a modification of the above preferred embodiment, the predetermined metric includes a quantification as to at least one of a dose distribution, a brachytherapy instrument location and a use of the brachytherapy instrument.

The revision approach(es) taken may rely on various quantitative metrics, including but not limited to metrics in relation to a dose distribution, metrics in relation to the location of a needle (as an example of a brachytherapy instrument) and metrics in relation to a needle itself, as part of the brachytherapy procedure.

In a variation of the above modification, the predetermined metric includes a quantification as to the dose distribution in taking into account at least one of an impact on an overall dose distribution and an impact on clinical objectives.

In particular a metrics in relation to the dose distribution may include (without being limited) an impact on overall dose distribution, e.g. a sum of difference in all dose voxels, an impact on all clinical objectives, e.g. in terms of decrease/increase in a D95 dose (a dose 95% of the region needs to receive), an impact on the clinical objectives of the target volume and an impact on the clinical objectives of the organs at risk.

In another variation of the above modification, the predetermined metric includes a quantification as to the brachytherapy instrument location taking into account the location of the brachytherapy instrument relative to at least one of a target volume, an organ at risk during the brachytherapy, another brachytherapy instrument and a imaging device provided to monitor the brachytherapy instrument.

A metric in relation to the location of the brachytherapy instrument (e.g. a needle), may include, but is not limited to considerations with respect to the target volume, with respect to the organs at risk, with respect to each other (e.g. maximize/minimize distance between consecutive ablation locations) and with respect to imaging devices (e.g. preserving image quality).

Maximizing the distance between needles may help fixating the tissue, thus preventing deformation, while minimizing the distance between needles increase the freedom in re-optimization of the dose plan for needles in another part of the target volume.

In a further variation of the above modification, the predetermined metric includes a quantification as to the use of the brachytherapy instrument taking into account at least one of a total dwelling time per instrument, a number of dwell positions per instrument and a number of radiation seeds per instrument.

The total dwelling time and the number of dwell positions are of particular concern in the context of HDR brachytherapy, while the number of seeds per needle (as an example of an instrument) is particularly relevant for LDR brachytherapy.

In yet another variation of the above modification, the predetermined metric includes a plurality of factors and a set of priorities for a relative weighing of the factors.

The metrics or portions thereof may be un-prioritized, yet may also be controlled by priorities, which are, for example, indicated by the user, such that e.g. needles affecting one particular organ at risk are placed first.

In another modification of the above preferred embodiment, the deviation calculation section is arranged to determine the deviation expectation of the treatment plan based on a simulation, wherein the simulation includes a predetermined amount of error in carrying out the not yet provided steps of the treatment plan.

In a further modification of the above preferred embodiment, the planning unit includes a permutation section for obtaining sequence permutations of the not yet provided steps of an unrevised treatment plan, wherein the planning unit is arranged to determine the revised treatment plan by selecting the sequence permutation providing the lowest deviation expectation.

According to the modification, just the order or sequence is revised, which allows for a minimization of computational effort involved with the revision.

In yet a further modification of the above preferred embodiment, the planning unit includes a variation section for obtaining dosage variations of the not yet provided steps of an unrevised treatment plan, wherein the planning unit is arranged to determine the revised treatment plan by selecting the dosage variation providing the lowest deviation expectation.

According to this modification, a margin around the previously providing dosing is considered, similarly allowing for a reduced effort in computation.

The above modifications may be combined, such that the sequence and the margin are considered together.

In a preferred embodiment, the additional receiving step, the revision step and the additional output step are carried out after provision of each step of the procedure, respectively.

Providing the updating repeatedly after each step or portion of the procedure is carried out allows for adjustments to be provided as soon as possible, thereby maximizing the chance of optimum results.

In a further aspect of the present invention a computer program is presented for assisting in a brachytherapy procedure, the computer program comprising program code means for causing a delivery assistance device according to the invention to carry out the steps of the method according to the invention when the computer program is run on the delivery assistance device.

It shall be understood that the delivery assistance device of claim 1, the delivery system of claim 12, the brachytherapy assistance method of claim 13, and the computer program of claim 15 have similar and/or identical preferred embodiments, in particular, as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
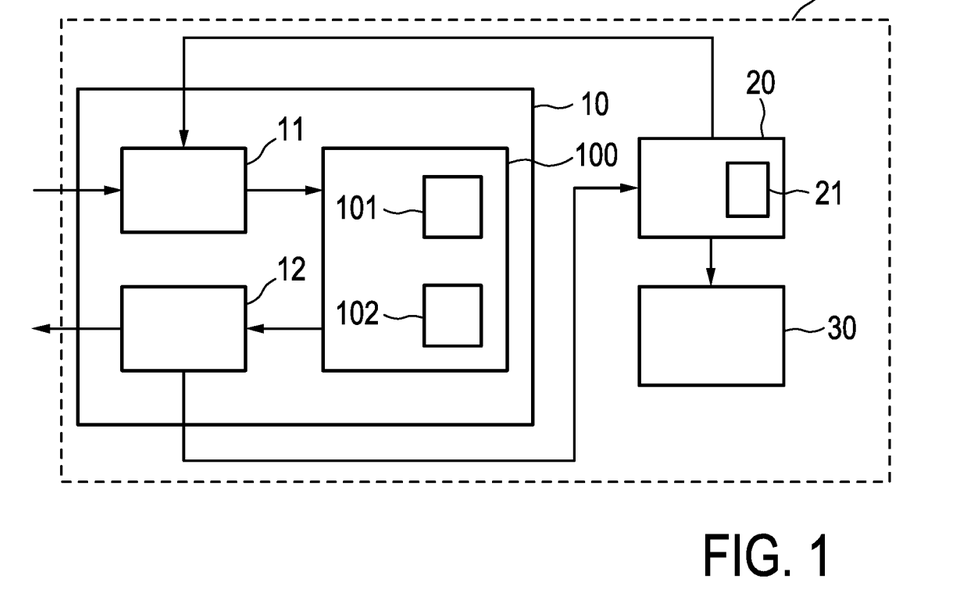
FIG. 1 shows a delivery system for brachytherapy including a delivery assistance device in accordance with an embodiment of the invention.

FIG. 1 shows a delivery system 1 for brachytherapy including a delivery assistance device 10 in accordance with an embodiment of the invention.

The delivery system 1 includes the delivery assistance device 10, a brachytherapy control device 20 and a plurality of brachytherapy instruments 30, i.e. needles for inserting the radioactive material into the body of the patient.

The brachytherapy control device 20 includes an imaging device 21, arranged to determine the position of each brachytherapy instrument when inserted into the body of the patient.

The delivery assistance device 10 includes an input unit 11, a planning unit 100 and an output unit 12.

The input unit 11 is arranged to receive, from outside of the system 1, information on a treatment objective of the brachytherapy procedure. Furthermore, the input unit 11 is coupled to the brachytherapy control device 20, so to receive information on already provided steps of the brachytherapy procedure. The input unit 11 forwards the information to the planning unit 100.

The planning unit is configured to determine a treatment plan based on the treatment objective and the already provided steps of the brachytherapy procedure, wherein the treatment plan includes dosage information and sequence information for further steps of the brachytherapy procedure.

The treatment plan determined by the planning unit 100 is provided to the output unit 12, which is configured to output the determined treatment plan to the brachytherapy control device 20 and to the outside of the system 1.

If no step of the brachytherapy procedure is already provided, i.e. in the initial stage of the procedure, the planning unit 100 is arranged to determine the treatment plan just based on the treatment objective.

In order to determine the treatment plan, the planning unit 100 includes an inverse optimization section 101 and a deviation calculation section 102. The inverse optimization section 101 is arranged to provide several solutions or candidates for a revised treatment plan based on the provided information, wherein the deviation calculation section 102 is arranged to determine respective deviation expectations for the candidates, such that the planning unit 100 may select the candidate having the lowest deviation expectation for being outputted as the revised treatment plan.

Figure 2:
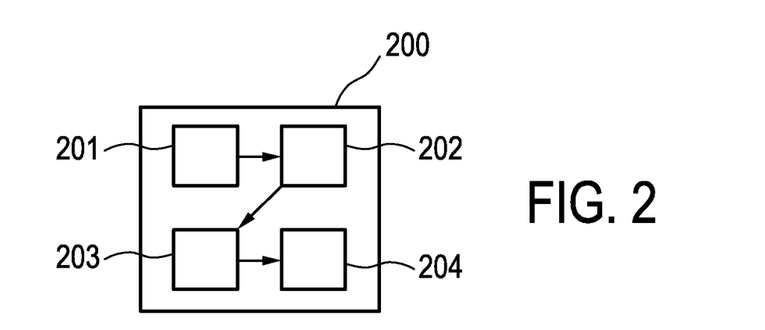
FIG. 2 shows a planning unit of a delivery assistance device in accordance with another embodiment of the invention.

FIG. 2 shows a planning unit 200 of a delivery assistance device in accordance with another embodiment of the invention. In FIG. 2, just the planning unit 200 of the delivery assistance device is shown, as other elements of the delivery system may remain unchanged in comparison to FIG. 1.

The planning unit 200 according to the present embodiment includes a calculation section 201, a difference determination section 202, a sub-plan determination section 203 and a deviation calculation section 204. The calculation section 201 is arranged for calculating a preliminary result from the information on already provided steps of the brachytherapy (see above). This information is provided by the calculation section 201 to the difference determination section 202, which is arranged to determine a difference between the preliminary result and the treatment objective to be achieved by the brachytherapy procedure. In other words, the difference determination section 202 determines the remaining portion of the treatment objective not yet achieved. The difference is provided to the sub-plan determination section 203, so to determine a treatment sub-plan by means of inverse optimization on the determined difference. This sub-plan is then provided to the deviation calculation section 204, so the deviation expectation of the sub-plan may be compared to other sub-plans determined based on slightly modified circumstances/constrains.

Figure 3:
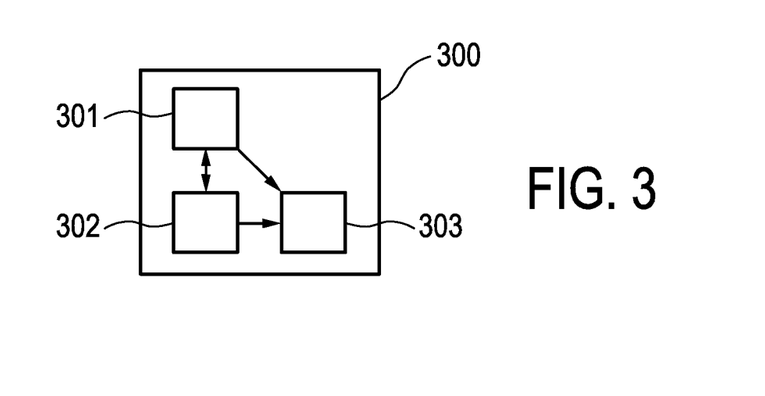
FIG. 3 shows a planning unit of a delivery assistance device in accordance with a further embodiment of the invention.

The planning unit 200 is further arranged to determine the revised treatment plan by replacing the dosage information and sequence information for not yet provided steps of the brachytherapy procedure according to the selected or determined treatment sub-plan. FIG. 3 shows a planning unit 300 of a delivery assistance device in accordance with a further embodiment of the invention.

Similar to FIG. 2, just the planning unit 300 is shown.

The planning unit 300 includes a permutation section 301, a variation section 302 and a deviation calculation section 303. The permutation section 301 is arranged to provide sequence permutations of the not yet provided steps of the current and unrevised treatment plan, while the variation section 302 is arranged for obtaining dosage variations of such steps, such that there is a "matrix" of permutations and variations providing changes on the unrevised treatment plan. This information is processed by the deviation calculation section 303 to enable the planning unit 300 to determine the revised treatment plan by selecting the combination of dosage variation and sequence permutation providing the lowest deviation expectation.

Figure 4:
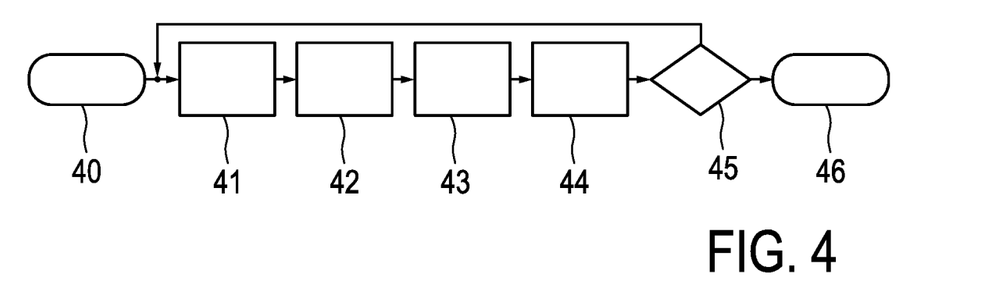
FIG. 4 shows a process diagram illustrating a needle placement process guided according to an embodiment of the invention.

FIG. 4 shows a process diagram illustrating a needle placement process guided according to an embodiment of the invention. In step 40, the procedure is started, leading to a first instance of an optimization step 41 for the dose plan, followed by an optimization step 42 for the needle sequence taking into consideration possible deviations due to mistakes in the placement or the like. This leads to a selection step 43 of selecting the next needle to be placed, which is then placed in a placement step 44. Following the placement step 44, there is checking step 45, in which it is determined whether or not the delivered dose already meets the desired treatment objective. If the treatment objective is not yet achieved, the process returns to the optimization step 41 of optimizing the dose plan in view of the already placed needle, followed by the other steps, as long as the checking step 45 results in a determination that the dose is not yet achieved. Once the desired dose is achieved, the procedure ends in step 46.

FIG. 5 shows exemplary displays of a needle guidance according to an embodiment of the invention.

Figure 5A:
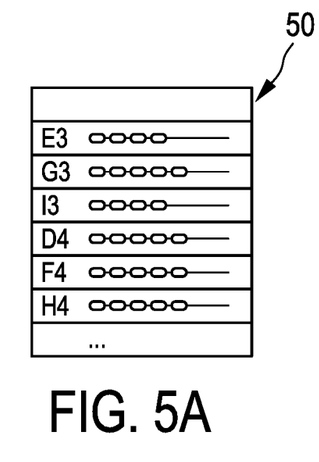
FIG. 5 shows exemplary displays of a needle guidance according to an embodiment of the invention.

Display 50 in FIG. 5a) shows the situation prior to any insertion of a needle and indicates that the first needle should be placed in grid hole E3, further illustrating the loading in the needles according to the current plan. The situation in FIG. 5b) is after the insertion of the needle in grid hole E3 (display 51), where it is now provided that the next needle to be placed will be placed in grid hole E4 (rather than originally in grid hole G3).

Figures 5B, 5C:
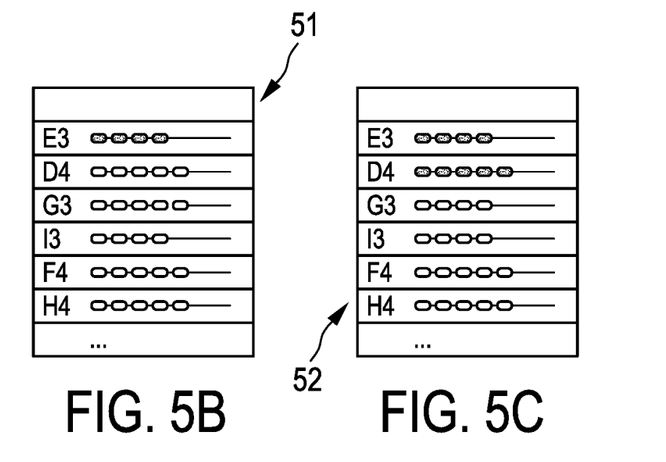

Following the insertion of the needle into grid hole D4, the sequence stays unmodified as illustrated in FIG. 5c), wherein, nevertheless, the loading in needle G3 is changed in comparison to the situation of FIG. 5a) and b) (see display 52).

Figure 6:
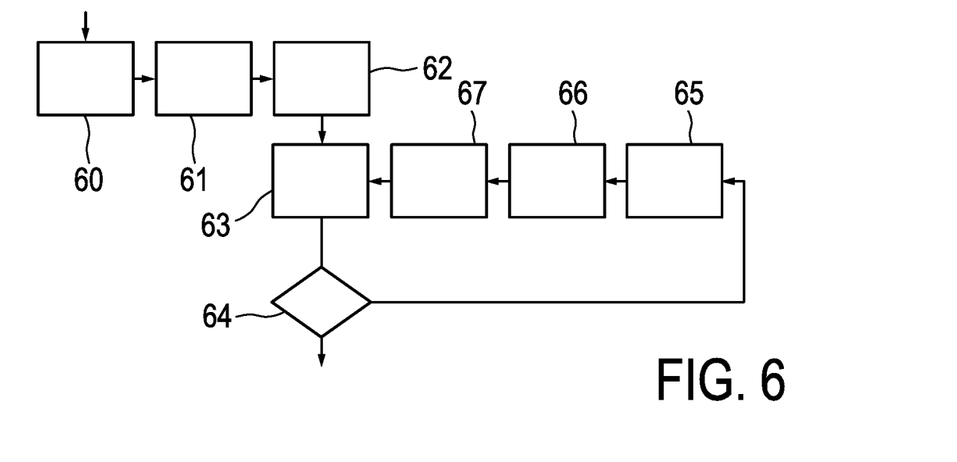
FIG. 6 shows a flow diagram illustrating a brachytherapy assistance method according to an embodiment of the invention.

FIG. 6 shows a flow diagram illustrating a brachytherapy assistance method according to an embodiment of the invention.

The method shown in FIG. 6 includes an initial receiving step 60 of receiving information on a treatment objective. This initial receiving step 60 is followed by a planning step 61, in which a treatment plan is determined based on the received information on the treatment objective. As mentioned before, the treatment plan includes dosage information and sequence information for steps of the brachytherapy procedure. In an initial output step 62 following the planning step 61, the determined treatment plan is outputted. This is followed by a brachytherapy step 63, in which a portion of the treatment plan determined in the planning step 61 is carried out. After this brachytherapy 63, there is a check 64 provided, in which it is determined whether the treatment objective is already achieved. If this would be the case, the process ends. Otherwise, the flow proceeds to an additional receiving step 65, in which information on already provided steps of the brachytherapy procedure is received. This additional receiving step 66 is followed by a revision step 66 of determining a revised treatment plan based on the received information, i.e. based on the treatment objective and the already provided steps of the brachytherapy procedure. The revised treatment plan, which might possibly be identical to the previous treatment plan is then outputted in an additional output step 67, leading to the next brachytherapy step 63.

The planning step 61 and the revision step 66 each include, respectively, determining the sequence information of the (revised) treatment plan so as to minimize an deviation expectation, indicating a deviation from the treatment objective to be expected, based on error expectation ranges of the (remaining) steps of the brachytherapy procedure. As long as the treatment objective is not achieved, the loop provided by steps 63, 64, 65, 66 and 67 is repeated.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims.

In an implementation of the invention, an assistance device comprises a planning unit, a needle sorting unit, a needle selection unit, and a display needle sequence display unit, capable of guiding the user to place needle is an optimal order. The optimal needle sequence may be determined while solving an inverse plan. The optimal needle sequence may be determined based on a provided plan. The optimal needle sequence may be determined based on a provided plan by simulating needle placement. The optimal needle sequence and the next needle may be determined based on the impact of needles on the dose distribution and clinical objectives with respect to target organs and organs at risk. The optimal needle sequence and the next needle may be determined based on the location of needles with respect to target organs, organs at risk, or other needles.

In the claims, the word "comprising" does not exclude other elements or steps, and the indefinite article "a" or "an" does not exclude a plurality.

A single processor, device or other unit may fulfill the functions of several items recited in the claims. The mere fact that certain measures are recited in mutually different dependent claims does not indicate that a combination of these measures cannot be used to advantage.

Operations like receiving, determining, outputting, calculating, and simulating can be implemented as program code means of a computer program and/or as dedicated hardware.

A computer program may be stored and/or distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A delivery system for a brachytherapy procedure, comprising:
   a delivery assistance device, comprising:
      an input unit arranged to receive information on a treatment objective;
      a planning unit arranged to determine a treatment plan based on the received information on the treatment objective, the treatment plan including dosage information for steps of the brachytherapy procedure; and an output unit arranged to output the treatment plan, wherein the treatment plan further includes sequence information for the steps of the brachytherapy procedure in the treatment plan indicating an order in which at least a subset of the steps of the brachytherapy procedure are to be carried out, wherein the planning unit is arranged to determine the sequence information so as to minimize a deviation expectation, indicating a deviation from the treatment objective to be expected, based on error expectation ranges of the steps of the brachytherapy procedure, wherein the input unit is further arranged to receive information on already provided steps of the brachytherapy procedure, wherein the planning unit is further arranged to determine a revised treatment plan based on the received information on the treatment objective and on the already provided steps of the brachytherapy procedure, and wherein the output unit is arranged to output the revised treatment plan;

a brachytherapy control device; and at least one brachytherapy instrument configured by the brachytherapy control device to deliver dosages to a patient based on the treatment plan and the revised treatment plan.

2. The delivery system of claim 1, wherein the planning unit includes:
 a calculation section for calculating a preliminary result from the information on already provided steps;
 a difference determination section for determining a difference between the preliminary result and the treatment objective; and
 a sub-plan determination section for determining a treatment sub-plan by means of inverse optimization on the determined difference,
 wherein the planning unit is arranged to determine the revised treatment plan by replacing the dosage information and sequence information for not yet provided steps of the treatment plan according to the treatment sub-plan.

3. The delivery system of claim 1, wherein the planning unit includes a deviation calculation section for calculating the deviation expectation for the treatment plan in view of the treatment objective according to a predetermined metric.

4. The delivery system of claim 3, wherein the predetermined metric includes a quantification as to at least one of a dose distribution, a brachytherapy instrument location and a use of the brachytherapy instrument.

5. The delivery system of claim 3, wherein the predetermined metric includes a quantification as to a dose distribution when determining at least one of an impact on an overall dose distribution and an impact on clinical objectives.

6. The delivery system claim 3, wherein the predetermined metric includes a quantification as to a brachytherapy instrument location taking into account the location of the brachytherapy instrument relative to at least one of a target volume, an organ at risk during the brachytherapy procedure, another brachytherapy instrument and a imaging device provided to monitor the brachytherapy instrument.

7. The delivery system of claim 3, wherein the predetermined metric includes a quantification as to use of a brachytherapy instrument taking into account at least one of a total dwelling time per instrument, a number of dwell positions per instrument and a number of radiation seeds per instrument.

8. The delivery system claim 3, wherein the predetermined metric includes a plurality of factors and a set of priorities for a relative weighing of the factors.

9. The delivery system of claim 3, wherein the deviation calculation section is arranged to determine the deviation expectation of the treatment plan based on a simulation, wherein the simulation includes a predetermined amount of error in carrying out not yet provided steps of the treatment plan.

10. The delivery system of claim 3, wherein the planning unit includes a permutation section for obtaining sequence permutations of not yet provided steps of an unrevised treatment plan, wherein the planning unit is arranged to determine the revised treatment plan by selecting the sequence permutation providing the lowest deviation expectation.

11. The delivery system of claim 3, wherein the planning unit includes a variation section for obtaining dosage variations of not yet provided steps of an unrevised treatment plan, wherein the planning unit is arranged to determine the revised treatment plan by selecting the dosage variation providing the lowest deviation expectation.

12. A software product for assisting in the brachytherapy procedure, the software product comprising program code means for causing a delivery assistance device according to claim 1 for assisting in the brachytherapy procedure when the software product is run on the delivery assistance device.

13. A brachytherapy delivery method for a brachytherapy procedure, comprising:
 an initial receiving step of receiving information on a treatment objective;
 a planning step of determining a treatment plan based on the received information on the treatment objective, the treatment plan including dosage information for steps of the brachytherapy procedure; and
 an initial output step of outputting the treatment plan, wherein the treatment plan further includes sequence information for the steps of the brachytherapy procedure in the treatment plan indicating an order in which at least a subset of the steps of the brachytherapy procedure are to be carried out, wherein the planning step includes determining the sequence information so as to minimize a deviation expectation, indicating a deviation from the treatment objective to be expected, based on error expectation ranges of the steps of the brachytherapy procedure, wherein the method further comprises, after at least one step of the brachytherapy procedure is provided:
 an additional receiving step of receiving information on already provided steps of the brachytherapy procedure;
 a revision step of determining a revised treatment plan based on the received information on the treatment objective and on the already provided steps of the brachytherapy procedure, wherein the revision step includes determining sequence information of the revised treatment plan so as to minimize the deviation expectation, indicating a deviation from the treatment objective to be expected, based on error expectation ranges of remaining steps of the brachytherapy procedure;
 an additional output step of outputting the revised treatment plan; and treatment steps of delivering dosages to a patient based on the treatment plan according to the initial output step and the revised treatment plan according to the additional output step.

14. The brachytherapy delivery method of claim 13, wherein the additional receiving step, the revision step and the additional output step are carried out after provision of each step of the brachytherapy procedure, respectively.

\* \* \* \* \*